US00PP34140P2

(12) United States Plant Patent
Bergman

(10) Patent No.: US PP34,140 P2
(45) Date of Patent: Apr. 19, 2022

(54) ***MANDEVILLA* PLANT NAMED 'MANZ0020'**

(50) Latin Name: ***Mandevilla sanderi* (Hemsl.) Woodson**
Varietal Denomination: MANZ0020

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/369,995

(22) Filed: Jul. 8, 2021

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
See application file for complete search history.

*Primary Examiner* — Susan McCormick Ewoldt
(74) *Attorney, Agent, or Firm* — Dale Skalla

(57) ABSTRACT

A new *Mandevilla* plant named 'MANZ0020' particularly distinguished by its large pure white flowers, glossy and smooth dark green foliage, bushy plant habit with a tendency to produce vines under low light growing conditions and with excellent branching and flower production and fast flowering response.

1 Drawing Sheet

Latin name of the genus and species of the plant claimed: *Mandevilla sanderi* (Hemsl.) Woodson.

Varietal denomination: 'MANZ0020'.

BACKGROUND OF THE NEW PLANT

The present invention comprises a new *Mandevilla*, botanically known as *Mandevilla sanderi*, and hereinafter referred to by the variety name 'MANZ0020'.

'MANZ0020' is a product of a planned breeding program. The new cultivar has large pure white flowers, glossy and smooth dark green foliage, bushy plant habit with a tendency to produce vines under low light growing conditions and with excellent branching and flower production and fast flowering response.

'MANZ0020' originates from a hybridization made in a controlled breeding program in Amatitlan, Guatemala. The pollinations were made in 2013.

The female parent was an unpatented, proprietary plant identified as 'DIP-190' and having large red flowers, a strong vining habit and slower flowering response.

The male parent of 'MANZ0020' was an unpatented, proprietary plant identified as 'DIP-195', with dark red flower color, larger foliage and slower flowering response.

The resulting seeds were sown in March 2014 and 'MANZ0020' was selected as one flowering plant within the progeny of the stated cross in December 2014 in a greenhouse in Gilroy, Calif.

The first act of asexual reproduction of 'MANZ0020' was accomplished when vegetative cuttings were propagated from the initial selection in February 2015 in a controlled environment in Gilroy, Calif.

BRIEF SUMMARY OF INVENTION

Horticultural examination of plants grown from cuttings of the plant initiated in June 2015 in Gilroy, Calif., and continuing thereafter, has demonstrated that the combination of characteristics as herein disclosed for 'MANZ0020' are firmly fixed and are retained through successive generations of asexual reproduction.

'MANZ0020' has not been observed under all possible environmental conditions. The phenotype may vary significantly with variations in environment such as temperature, light intensity and day length.

A Plant Breeder's Right for this cultivar has not yet been applied for. 'MANZ0020' has not been made publicly available prior to the effective filing date of this application, notwithstanding any disclosure that may have been made less than one year prior to the effective filing date of this application by the inventor or another who obtained 'MANZ0020' directly from the inventor.

The following traits have been repeatedly observed and are determined to be basic characteristics of the new variety. The combination of these characteristics distinguishes this *Mandevilla* as a new and distinct variety.

BRIEF DESCRIPTION OF THE PHOTOGRAPHS

Figure 1:
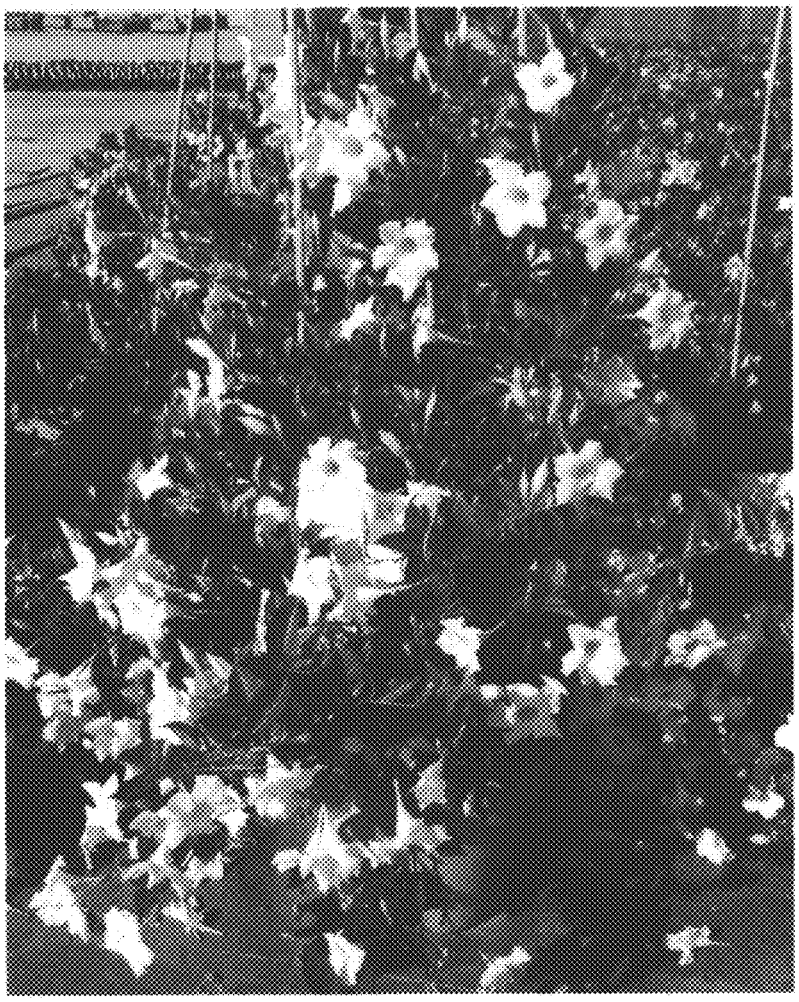
Figure 2:
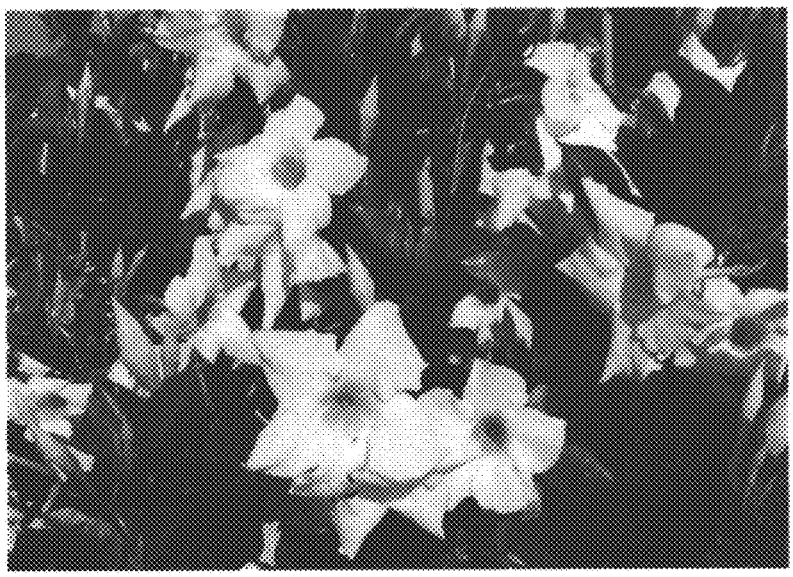

The accompanying photographic drawings show typical flower and foliage characteristics of 'MANZ0020' with colors being as true as possible with an illustration of this type. The photographic drawings show in FIG. 1, a flowering potted plant of the new variety and in FIG. 2, a close-up of the flowers.

DETAILED BOTANICAL DESCRIPTION

The aforementioned photographs were taken in September 2016 in Gilroy, Calif. The plants were growing in large pots outdoors; they were about 6 months in age.

TABLE 1

DIFFERENCES BETWEEN THE NEW VARIETY 'MANZ0020' AND A SIMILAR VARIETY

| | 'MANZ0020' | 'FISRIX WHIT' (Not patented) |
|---|---|---|
| Foliage size: | Smaller | Larger |
| Foliage color: | Darker | Lighter |
| Flowering response: | Faster | Slower |

Plant:

*Form, growth, and habit.*—Perennial or sub-shrub, herbaceous younger stems, woody at base of older stems, semi-upright, with moderate tendency of developing vines depending on season and light intensity. Time for producing a commercial, flowering plant approximately is 12 weeks for one plant in a quart size container.

*Plant height.*—32 cm.

*Plant height (inflorescence included).*—32 cm.

*Plant width.*—23 cm.

Roots:

*Number of days to initiate roots.*—About 16-20 days at about 22 degrees C.

*Number of days to produce a rooted cutting plant.*—5 weeks at about 22 degrees C.

*Type.*—Fibrous, a little fleshy, free branching.

*Color.*—RHS N1558D.

Foliage:

*Arrangement of leaves.*—Simple leaf, opposite and decussate.

*Immature leaf, color upper surface.*—RHS 137B.

*Immature leaf, color lower surface.*—RHS 146B.

*Mature leaf, color upper surface.*—RHS 139A.

*Mature leaf, color lower surface.*—RHS 147B.

*Length.*—6.8-7.5 cm.

*Width.*—3.6-4.6 cm.

*Shape.*—Ovate.

*Base shape.*—Rounded.

*Apex shape.*—Cuspidate to acuminate.

*Margin.*—Entire.

*Texture, upper surface.*—Smooth, glossy, glabrous.

*Texture, lower surface.*—Smooth, glossy, glabrous.

*Pattern of leaf veins.*—Pinnate.

*Color of veins, upper surface.*—RHS 138B.

*Color of vein (midrib), lower surface.*—RHS 144D.

*Petiole color.*—RHS 138B.

*Length.*—0.6-1.3 cm.

*Diameter.*—0.2-0.25 cm.

*Petiole, texture.*—Glabrous.

Stem:

*Branching characteristics.*—Moderately free branching.

*Quantity of main branches per plant.*—3-4.

*Color of stem.*—RHS 146C.

*Length of stem.*—25-28 cm.

*Diameter (at about mid-point).*—0.35 cm.

*Length of internodes.*—2.3-2.7 cm.

*Stem, texture.*—Smooth and glabrous.

Inflorescence:

*Type of inflorescence.*—Raceme of several flowers, emerging from nodes of the stem.

*Number of flowers per inflorescence.*—7-9.

*Blooming habit.*—Continuously through the summer months.

*Quantity of flowers per plant.*—About 8 in various stages of development.

*Lastingness of individual blooms on the plant.*—Approximately 8-10 days, depending on temperature.

*Fragrance.*—Absent.

*Peduncle.*—

*Color.*—Green, RHS 146C.

*Length.*—2.2-2.5 cm.

*Diameter.*—0.25 cm.

*Texture.*—Smooth, glabrous, somewhat glossy.

Bud (just before opening/showing color):

*Color.*—Closest to RHS 145D with irregular tones of RHS 66D.

*Length.*—7.3 cm.

*Width.*—1.6 cm.

*Shape.*—Elongated, spindle shape.

Immature flower:

*Diameter.*—7.5 cm.

*Vertical diameter.*—About 6.5 cm.

*Color upper surface.*—RHS 155D.

*Color lower surface.*—RHS 155D.

Mature flower:

*Shape.*—Funnelform, funnel shaped base, formed by 5 partly fused petals, with the petal lobes opening outwards, and a little overlapping.

*Flower, horizontal diameter.*—8.7-9.0 cm.

*Flower, vertical diameter.*—About 6.5 cm.

*Flower, diameter of the funnel.*—1.6 cm.

*Flower color, general.*—White.

*Flower color, upper surface.*—RHS 155D.

*Flower color, lower surface.*—RHS 155D.

*Color of the funnel, inner side.*—Closest to RHS 9A.

*Color of the funnel, outside.*—RHS 145C.

*Petal, shape.*—Roughly ovate, asymmetric.

*Petal apex shape.*—Cuspidate.

*Petal base shape.*—Fused.

*Petal margin.*—Mainly entire and mildly undulate.

*Petal length, from the corolla opening.*—4.0 cm.

*Petal width, maximum.*—4.4 cm.

*Corolla, texture of upper surface.*—Glabrous, papillose.

*Corolla, texture of lower surface.*—Glabrous, papillose.

*Pedicel, color.*—Light green, RHS 146C.

*Length.*—1.8-2.1 cm.

*Diameter.*—0.25 cm.

*Pedicel, texture.*—Smooth, glabrous.

Calyx:

*Form.*—5 sepals, closely attached to the base of the flower.

*Color, visible outer surface.*—RHS 146C.

*Length.*—1.0 cm.

*Width.*—0.45 cm.

*Shape.*—Subulate.

*Apex shape.*—Acute.

*Base.*—Fused.

*Margins.*—Entire.

*Texture, upper surface.*—Glabrous.

Reproductive organs:

Gynoecium:

*Pistil.*—1, with a 5-lobed stigma.

*Style length.*—2.3 cm.

*Diameter.*—0.05 cm.

*Style color.*—RHS 150D.

*Stigma color.*—RHS 144C.

*Stigma shape*.—Five lobed.

*Ovary color*.—RHS 144B.

Androecium:

*Stamens*.—5, surrounding the style and stigma.

*Filaments*.—Fused with the base of the flower.

*Anther*.—Elongated.

*Anther color*.—RHS 162B.

*Anther length*.—1.2 cm.

*Color of pollen*.—RHS 4D.

*Pollen amount*.—Moderate.

Fertility/seed set: Has not been observed on this hybrid.

Disease/pest resistance: Has not been observed on this hybrid.

What is claimed is:

1. A new and distinct variety of *Mandevilla* plant named 'MANZ0020' substantially as illustrated and described herein.

* * * * *